United States Patent [19]

Jørgensen

[11] Patent Number: 5,647,848
[45] Date of Patent: Jul. 15, 1997

[54] HIGH STRENGTH LOW COMPLIANCE COMPOSITE BALLOON FOR BALLOON CATHETERS

[75] Inventor: Ole Jørgensen, Lyngby, Denmark

[73] Assignee: Meadox Medicals, Inc., Oakland, N.J.

[21] Appl. No.: 487,177

[22] Filed: Jun. 7, 1995

[51] Int. Cl.⁶ ............................................ H61M 29/00
[52] U.S. Cl. ........................ 604/96; 604/282; 606/194
[58] Field of Search .................... 604/96–103, 280–282; 606/194

[56] References Cited

U.S. PATENT DOCUMENTS

| | | |
|---|---|---|
| 4,024,873 | 5/1977 | Antoshkiw et al. . |
| 4,448,195 | 5/1984 | Le Veen et al. . |
| 4,637,396 | 1/1987 | Cook . |
| 4,706,670 | 11/1987 | Andersen et al. . |
| 4,737,153 | 4/1988 | Shimamura et al. . |
| 4,796,629 | 1/1989 | Grayzel . |
| 4,896,669 | 1/1990 | Bhate et al. . |
| 5,021,043 | 6/1991 | Becker et al. . |
| 5,041,093 | 8/1991 | Chu . |
| 5,192,296 | 3/1993 | Bhate et al. . |
| 5,201,706 | 4/1993 | Noguchi et al. . |
| 5,209,725 | 5/1993 | Roth . |
| 5,314,443 | 5/1994 | Rudnick . |
| 5,330,429 | 7/1994 | Noguchi et al. . |
| 5,358,486 | 10/1994 | Saab . |
| 5,358,487 | 10/1994 | Miller . |
| 5,364,357 | 11/1994 | Aase . |
| 5,454,795 | 10/1995 | Samson et al. . |

FOREIGN PATENT DOCUMENTS

| | | |
|---|---|---|
| 1092161 | 11/1960 | Germany . |
| 1566674 | 5/1980 | United Kingdom . |
| 2130093 | 5/1984 | United Kingdom . |

OTHER PUBLICATIONS

P.M. Adams and G. Farrow, *Processing, Properties And Applications Of Fibers From Fully Aromatic Polyesters*, Hoechst Celanese Corporation (undated).

Advertisement entitled *High Performance Resins–A Breakthrough In High–Performance Thermoplastics*, Celanese Limited (undated).

Primary Examiner—Michael Buiz
Assistant Examiner—Bhisma Mehta
Attorney, Agent, or Firm—Hoffmann & Baron

[57] ABSTRACT

An improved dilation balloon for securement to a catheter. The balloon includes an elastomeric skin having a constraining structure affixed thereto. The constraining structure allows radial expansion between an uninflated diameter $D_{defL}$ and an inflated diameter $D_{infL}$. The minimum inflation pressure can be calculated based on the chosen elastomer $D_{infL}$ and $D_{defL}$.

9 Claims, 4 Drawing Sheets

HIGH STRENGTH LOW COMPLIANCE COMPOSITE BALLOON FOR BALLOON CATHETERS

BACKGROUND OF THE INVENTION

The present invention relates to balloon catheters and, more particularly, to an elastomeric balloon configured to expand to a predetermined diameter upon application of a predetermined pressure thereto.

Balloon catheters are well known in the art. Such catheters are employed in a variety of medical procedures, including dilation of narrowed blood vessels, placement of stents and other implants, temporary occluding of blood vessels, etc.

In a typical application, the balloon is advanced to the desired location in the vascular system. The balloon is then pressure-expanded in accordance with a medical procedure. Thereafter, the pressure is removed from the balloon, allowing the balloon to contract and permit removal of the catheter. It is to be appreciated that the balloon must be formed of an elastomeric material which is readily pressure-expanded, yet will also readily contract upon removal of the inflation pressure.

Procedures such as these are generally considered non-invasive, and are often performed in a manner which minimizes disruption to the patient's body. As a result, catheters are often inserted from a location remote from the region to be treated. For example, during angioplasty procedures involving coronary vessels, the balloon catheter is typically inserted into the femoral artery in the groin region of the patient, and then advanced through such vessel into the coronary region of the patient. These catheters typically include some type of radiopaque marker to allow the physician performing the procedure to monitor the progress of the catheter through the body. However, because the balloon portion of the catheter is not visible to the physician, such balloon may be overexpanded during inflation without the physician's awareness.

Attempts have been made in the past to control and limit overexpansion of catheter balloons. One improved balloon is disclosed in U.S. Pat. No. 4,706,670. The balloon of the '670 patent, along with the catheter tubing, is reinforced by continuous helical filaments which repeatedly cross each other. The filaments are formed as a braid which are embedded or otherwise encased in the yielding plastic material. The filaments are arranged such that prior to pressurization of the balloon, the filaments of the balloon portion lie at an angle which is less than a neutral angle of 54.73° relative to the axis of the balloon. As the balloon is inflated, the angle of the filaments in the wall of the balloon approach the mentioned neutral angle. This neutral angle represents the equilibrium point of the balloon at which point the circumferential stresses in the balloon balance the axial stresses in the balloon, such that a further increase in the internal pressure of the catheter will not produce any further increase in the diameter of the balloon.

Under ideal conditions, the balloon would reach its maximum diameter at the point where the reinforcing fibers reach their neutral angle. However, due to limitation in the materials and to interaction between the elastomer and the reinforcing fibers, the actual performance of the balloon will vary. For example, the reinforcing fibers are typically extensible to some degree, allowing the balloon to continue expanding even after the filaments reach their neutral angle. Moreover, the reinforcing fibers employed in the balloon may soften as the balloon is repeatedly inflated and deflated, again allowing the balloon to overexpand upon inflation. The reinforcing fibers and the balloon may also interact in a manner which introduces undesirable torsional moments into the balloon. Finally, the elastomeric properties of the balloon may cause such balloon to "bulge" through the open regions between the reinforcing fibers.

Accordingly, there is a need in the art for a reinforced elastomeric balloon having a predefined maximum expanded diameter. This maximum expanded diameter should remain constant even as the pressure of the balloon is increased. Moreover, this maximum expanded diameter should remain constant upon repeated inflation and deflation of the balloon. The pressure required to reach maximum expansion should be calculatable based on the chosen elastomer and the diameter of the expanded and unexpanded balloon. Finally, the reinforcing structure should be configured to reduce unwanted forces transferred between the reinforcing structure itself and the elastomer during the inflation procedure.

SUMMARY OF THE INVENTION

The present invention, which addresses the needs of the prior art, provides a balloon for securement to a catheter. The balloon includes an elastomeric generally hollow pressure expandable body having a wall thickness of t and being expandable under an internally applied minimum working pressure P from an unexpanded diameter $D_{defl}$ to an expanded diameter $D_{infl}$. The elastomeric body has a secant modules $E_{sec}$ where $$E_{sec} = \frac{\sigma(\epsilon_{infl})}{\epsilon_{infl}}$$

where $\sigma(\epsilon_{infl})$ is the nominal uniaxial tension in the body as a function of $\epsilon_{infl}$ and $$\epsilon_{infl} = \frac{D_{infl}}{D_{defl}}.$$

The balloon further includes a substantially non-compliant expandable constraining structure affixed to the elastomer. The constraining structure limits expansion of the body to a maximum diameter of $D_{infl}$ wherein the minimum working pressure P required to expand the body to a diameter no greater than $D_{infl}$ is defined by the equation:

$$\frac{P \cdot D_{defl}}{2 \cdot E_{sec} \cdot t} \geq 1$$

In one preferred embodiment, $E_{sec}$ is less than about 7 MPa at 500% elongation as measured in accordance with ASTM D412-87. The constraining structure is preferably formed of fibers having an elongation to break of less than about 10% and a tensile strength greater than about 1 GPa.

As a result, the balloon of the present invention is fully inflated and non-compliant when the criteria, noted herein as the J criteria, is fulfilled. The criteria states that, provided that the applied pressure is beyond the level that balances the uniaxial tension in a corresponding pure elastomeric ring at the nominal diameter, than the balloon is essentially fully inflated. Thus, the minimum inflation pressure can be readily calculated based on the S—S curve for the elastomeric material, the degree of stretch that the balloon design describes and the thickness of the balloon skin.

DETAILED DESCRIPTION OF THE INVENTION

Figure 1:
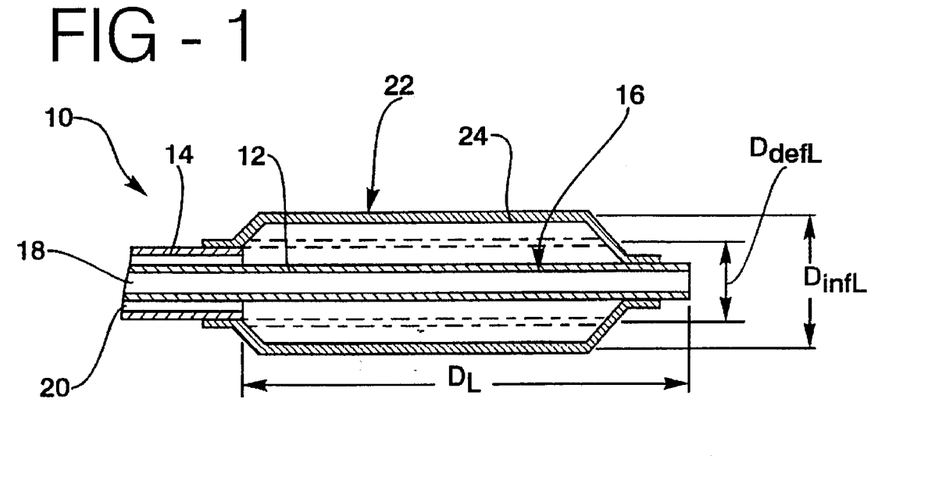
FIG. 1 is a sectional view of a distal portion of a catheter.

Referring to FIG. 1, catheter 10 includes concentrically arranged tubes 12 and 14. Tube 12, the inner tube, extends from a proximal end of the catheter (not shown) to a distal end 16 of the catheter. Tube 12 provides a lumen 18 for advancement of a guidewire (not shown) therethrough. Tube 14, the outer tube, also extends from the proximal end of the catheter, but terminates a distance $D_1$ from distal end 16. An inflation lumen 20, which extends from the proximal end of the catheter, is defined between the outer diameter of inner tube 12 and the inner diameter of outer tube 14.

A balloon 22 formed of an elastomeric skin 24 is secured to the tubes of the catheter. As shown, the proximal end of the balloon is secured to the outer diameter of tube 14, while the distal end of the balloon is secured to the outer diameter of tube 12. Balloon 22 is shown in its fully expanded state. Inflation lumen 20, which is in fluid communication with the interior volume of the balloon, allows such balloon to be inflated from a diameter $D_{defl}$ (non-inflated) to a diameter $D_{infl}$ (fully inflated).

Figure 2:
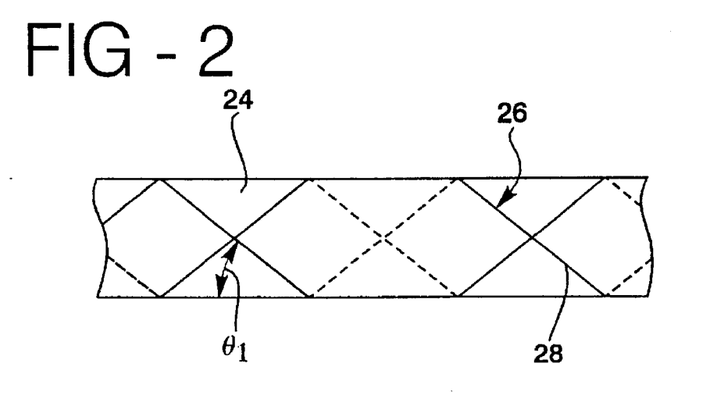
FIG. 2 is a portion of the elastomeric skin of the balloon in an unexpanded state.
Figure 3:
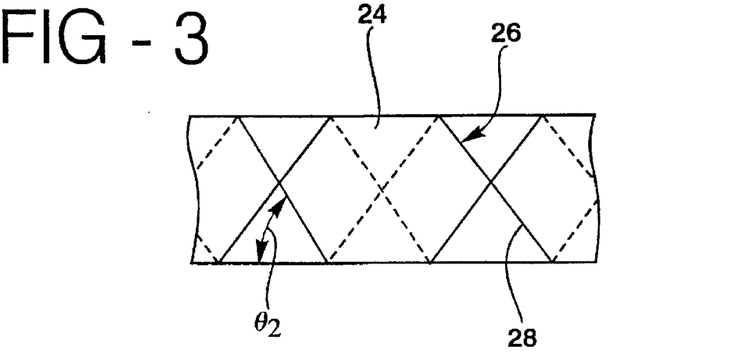
FIG. 3 is a portion of the elastomeric skin of the balloon in an expanded state.

Referring to FIGS. 2 and 3, a constraining structure 26 is affixed to skin 24. Preferably, structure 26 is embedded or otherwise affixed to elastomeric skin 24. This constraining structure allows unrestrained expansion of the balloon from $D_{defl}$ to $D_{infl}$, but effectively restrains the balloon from undergoing any radial expansion beyond $D_{infl}$.

Structure 26 is preferably formed of helically extending fibers 28. In turn, these fibers are preferably formed of bundles of continuous monofilaments. Aramide, polyethylene, steel, polyester, glass, carbon and ceramics are preferred materials. Fibers made of liquid crystal polymers, such as VECTRAN, are particularly preferred. In one preferred embodiment, the filaments have a thickness of less than about 15 µm and constitute from about 20% to about 50% by volume of the walls of the balloon.

As disclosed in U.S. Pat. No. 4,706,670, incorporated herein by reference, a system of reinforcing fibers may be imbedded or otherwise encased in the elastomeric skin of the balloon. These fibers helically extend throughout the balloon. The fibers are positioned in the elastomer such that the fibers lie at an angle which is less than a neutral angle of 54.73° relative to the axis of the balloon when the balloon is unpressurized. FIG. 2 depicts balloon 22 in an unpressurized state and, accordingly, angle $\theta_1$ is less than the neutral angle. FIG. 3 depicts balloon 22 in a pressurized and fully expanded state and, accordingly, angle $\theta_2$ is equal to the neutral angle.

As the system of fibers is radially expanded (due to inflation of the balloon), the fibers reorient themselves with respect to one another until the aforementioned neutral angle is reached. At this point, constraining structure 26 has reached a point of equilibrium where the circumferential stresses in the balloon balance the axial stresses in the balloon. More specifically, structure 26 has reached a condition of maximum radial expansion (as shown in FIG. 3). Constraining structure 26, because it is affixed to the balloon skin, thus prevents the balloon from undergoing any further radial expansion.

Without the balloon skin, the fibers would orient themselves to the neutral angle with a minimum of internal pressure. When an elastomeric skin is added to the arrangement, the skin, to some degree, interferes with the fiber's ability to reorient to the neutral angle. As a result, it has been difficult in the past to determine when a balloon is fully expanded and, more particularly, to predict the elasticity needed in the elastomer to allow such elastomer to properly expand, without negatively impacting the reorienting fibers.

Figure 4:
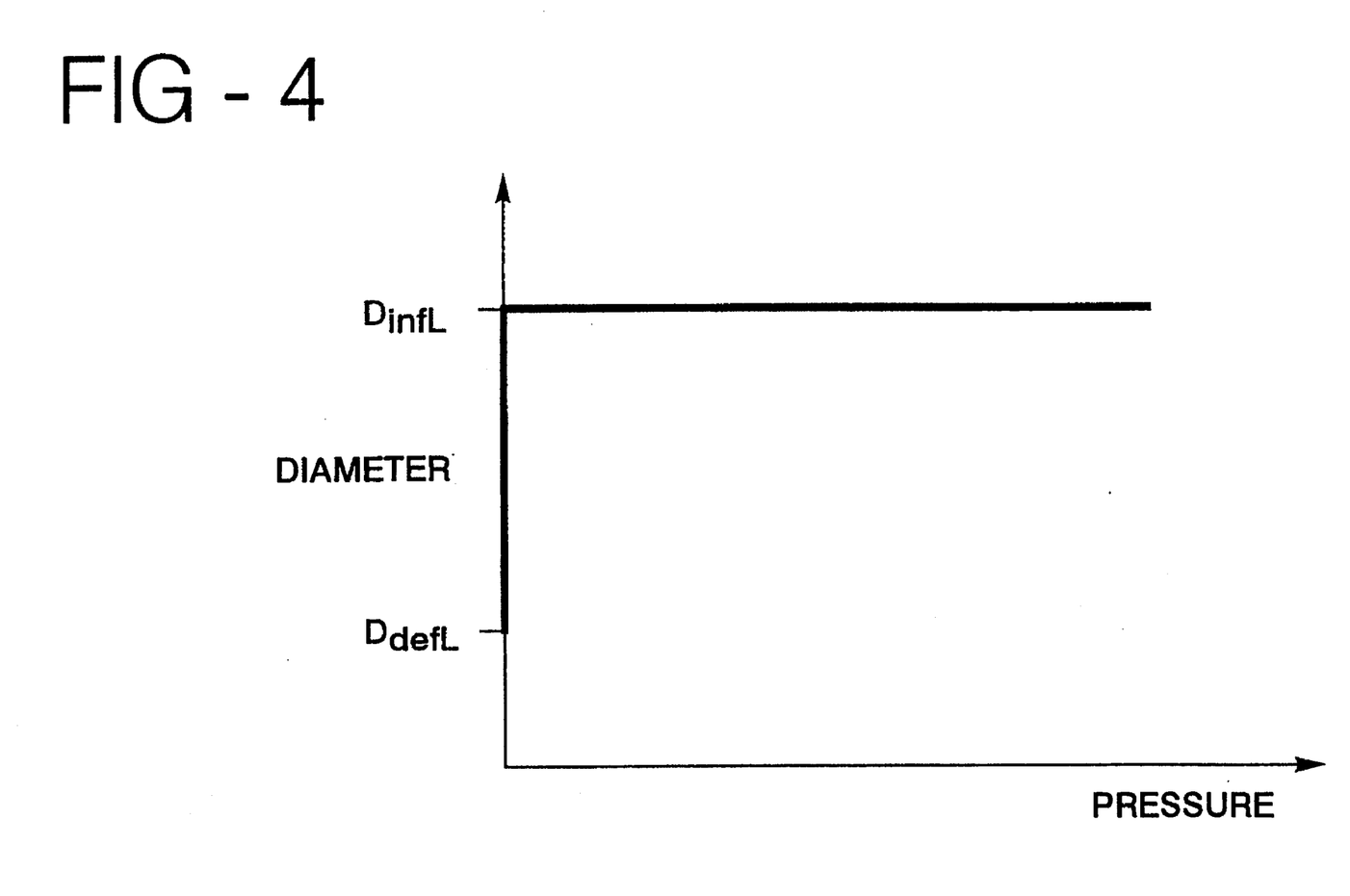
FIG. 4 is a graphical representation of diameter vs. pressure for an ideal balloon.

Fibers 28 undergo rigid body motion during the initial expansion of the balloon, i.e., the fibers simply reorient themselves at the points of crossing. Ideally, the fibers are invisible to the elastomeric skin of the balloon during this initial expansion. Once the fibers have oriented themselves such that the angle between the fibers and the longitudinal axis of the balloon reaches the neutral angle, the fibers are in a state of equilibrium. At this point, the fibers are carrying the load and the effects of the elastomeric skin become invisible to the balloon. Ideally, the fibers are sufficiently inextensible such that increases in the internal working pressure within the balloon do not result in additional radial expansion of constraining structure 26 (and thus the elastomeric skin). The inflation characteristics of a balloon having an ideally compliant elastomeric skin and ideally rigid fibers is shown in FIG. 4.

The fully inflated balloon has a compliance that is essentially determined by the compliance of the fibers. Hence, with the utilization of rigid fibers, the balloon will be non-compliant in its fully inflated state. In one embodiment, the fibers are designed to have a rigidity which is several orders of magnitude greater than that of the elastomer.

This difference in rigidity, although desirable with respect to independent movement of the components of the balloon, can introduce unwanted torsional moments into the elastomeric balloon depending upon the construction of the balloon and the fibers. More specifically, in the prior art balloons having plural reinforcing helical fibers affixed thereto, the fibers are typically arranged in two crossing helices (spiralling in opposite directions) where one helix is radially spaced from the other helix. Upon expansion of the balloon, the outer layer carries the tensile load in one direction while the inner layer carries a load in the other direction. Thus, with respect to an imaginary midplane between the two helices, a torsional moment is created between the two helices during expansion of the balloon. This may cause the elastic matrix, i.e., the balloon skin, to undergo unwanted twisting and, at times, may even result in failure of the material.

In order to minimize the torsional moments created by the unbalanced helices, in one embodiment of the present invention, the fibrous reinforcement preferably includes a single layer of braided, knitted or woven fibers which is capable of providing the desired reinforcement while eliminating risk of breakage of the elastomeric material. The fibrous reinforcement may also consist of three or more helically extending layers of fibers.

The reinforcement may include, for example, four layers of helically extending filaments. The inner and outer layers preferably have the same winding direction, while the two intermediate layers have the opposite winding direction.

Further, the fibrous reinforcement may comprise three layers of helically extending filaments, the inner and outer layers having the same winding direction and the intermediate layer having an opposite winding direction and being of double thickness.

In any of the above multiple layer situations the spirals or helices are constructed to be balanced with respect to an imaginary midplane between the layers.

As mentioned, the skin of balloon 22 is preferably formed of an elastomeric material which readily allows expansion upon application of an internal working pressure thereto. This elastomeric material should also be sufficiently elastic to allow the balloon to readily contract upon removal of the inflation pressure from the balloon. Finally, the elastomeric material must not be so flexible so as to allow the material to "bulge" through the open regions between the fibers 28.

It has been discovered herein that a catheter balloon can be produced wherein the minimum inflation pressure necessary to fully expand the balloon can be determined based on the elastomer used for the balloon skin, the maximum predefined inflation diameter of the balloon (defined by constraining structure 26) and the diameter of the deflated balloon. As a result, a physician choosing a particular balloon catheter is advised of the minimum inflation pressure. The physician is therefore confident, once the balloon has been inflated to the defined minimum inflation pressure, that such balloon has been fully expanded.

Moreover, the physician need not worry about overinflating the balloon. With the balloon catheters of the prior art, the minimum pressure at which the balloon was fully expanded could not be readily predicted. As a result, there was a tendency to overpressurize the balloon to ensure that such balloon had actually inflated to its full working diameter. This introduced the possibility of i) overexpansion of the balloon beyond its defined maximum working diameter, ii) softening and stretching of the balloon structure such that subsequent inflations of the balloon would result in overexpansion, and iii) rupture risks.

In order to quantify the influence of the constitutive behavior of the elastomer, a criteria, denoted herein as the J criteria, is presented. When fulfilled, the criteria defines the lower bracket of the pressure range within which an essentially fully inflated and non complaint balloon is evident. The criteria states that, provided that the applied pressure is beyond the level that balances the uniaxial tension in a corresponding pure elastomeric ring at the nominal diameter, then the balloon is essentially fully inflated. Stated differently, for a fixed balloon design, the J criteria determines the dimensionless pressure above which the balloon is fully inflated and hence the non-compliance of the fibers results in non-compliant balloon performance. Hence, the criteria refers to the S-S curve of the elastomeric material, the degree of stretch that the balloon design prescribe, the thickness of the balloon skin and the working pressure range.

Particularly, it has been discovered herein that if a balloon is manufactured such that its J-factor is greater than or equal to 1, the minimum pressure required for full expansion is defined as follows:

$$J = \frac{P \cdot D_{defl}}{2 \cdot E_{sec} \cdot t} \geq 1$$

wherein P is the internal working pressure expressed in MPa, $D_{defl}$ is the diameter of the deflated balloon expressed in mm, t is the wall thickness of the balloon skin expressed in mm, and $E_{sec}$ is the secant modules of the elastomer.

Figure 5:
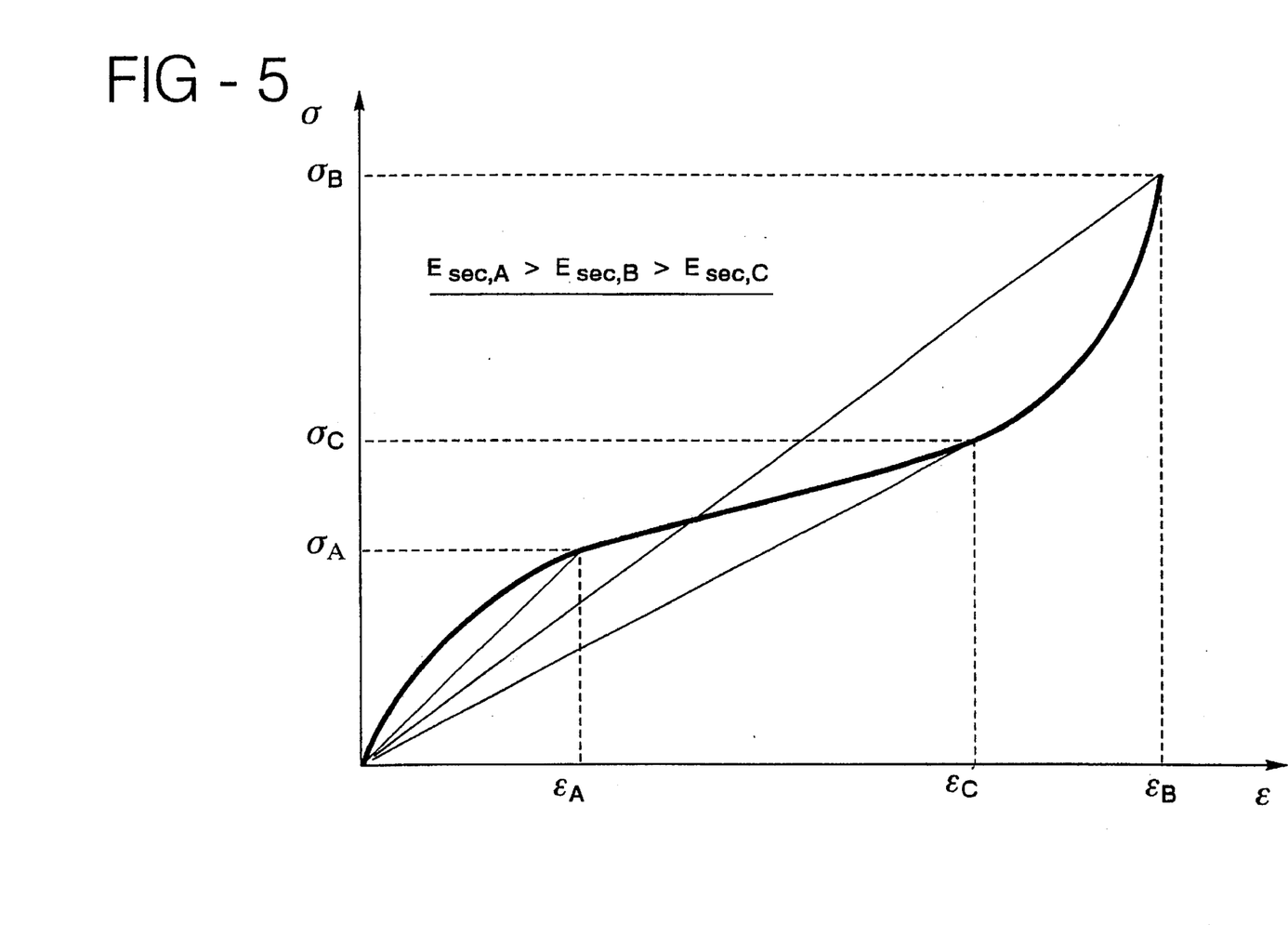
FIG. 5 is a graphical representation of stress vs. elongation for a given elastomer.

The S—S curve for a particular elastomer may be determined by means of mechanical testing. A strip of known cross-sectional area is subjected to a tensile test according to ASTM D412-87. The tensile force is determined as a function of the elongation of the strip. Based on such values, the nominal inflated stress σ (force divided by the initial cross-sectional area) and the relative extension ε are calculated. A curve depicting the relationship between the two parameters is then prepared. An S-shaped curve, such as the curve illustrated in FIG. 5, will typically be produced. The secant modules at a relative extension corresponding to a point on the curve is determined by the inclination of the straight line from the origin through such point.

Mathematically, the secant modules, $E_{sec}$, is defined as follows:

$$E_{sec} = \frac{\sigma(\epsilon_{infl})}{\epsilon_{infl}}$$

wherein $\sigma(\epsilon_{infl})$ represents the nominal uniaxial tension in the elastomer as a function of $\epsilon_{infl}$, and $$\epsilon_{infl} = \frac{D_{infl}}{D_{defl}}$$

wherein $D_{infl}$ designates the predefined maximum inflation diameter of the expanded balloon and $D_{defl}$ designates the inner diameter of the non-expanded balloon.

If the matrix material consists of more than one elastomer, e.g. N elastomers, the secant modules is calculated on the basis of the following equation:

$$E_{sec} = \sum_{i=1}^{N} E_{sec,i} \cdot \frac{V_i}{V_{total}}$$

wherein i designates elastomer number i and $V_i/V_{total}$ defines the volume fraction of said component.

In one preferred embodiment, the elastomeric material has a secant modules of less than about 7 MPa at 500% elongation as measured in accordance with ASTM D412-87. Preferably, the internal working pressure is within the range of about 0.4 MPa to about 1.2 MPa.

EXAMPLE

To exemplify the utilization of the J criteria the inflation characteristics of one specific balloon is set forth below:

A balloon catheter comprising a balloon having a wall thickness t of 0.2 mm was made from an elastomer having a secant modules, $E_{sec}$, of 1.6 MPa, a $D_{defl}$ of 1.58 mm, and a $D_{infl}$ of 9.8 mm. The fibers had an elongation to break of less than 3%. A working pressure of 1.2 MPa is proposed.

The minimum inflation pressure P necessary to obtain a J value equal to or greater than 1 was calculated as follows:

$$\frac{P \cdot 1.58}{2 \cdot 1.6 \cdot 0.2} \geq 1, \quad P = 0.4 \text{ MPa}$$

Figure 6:
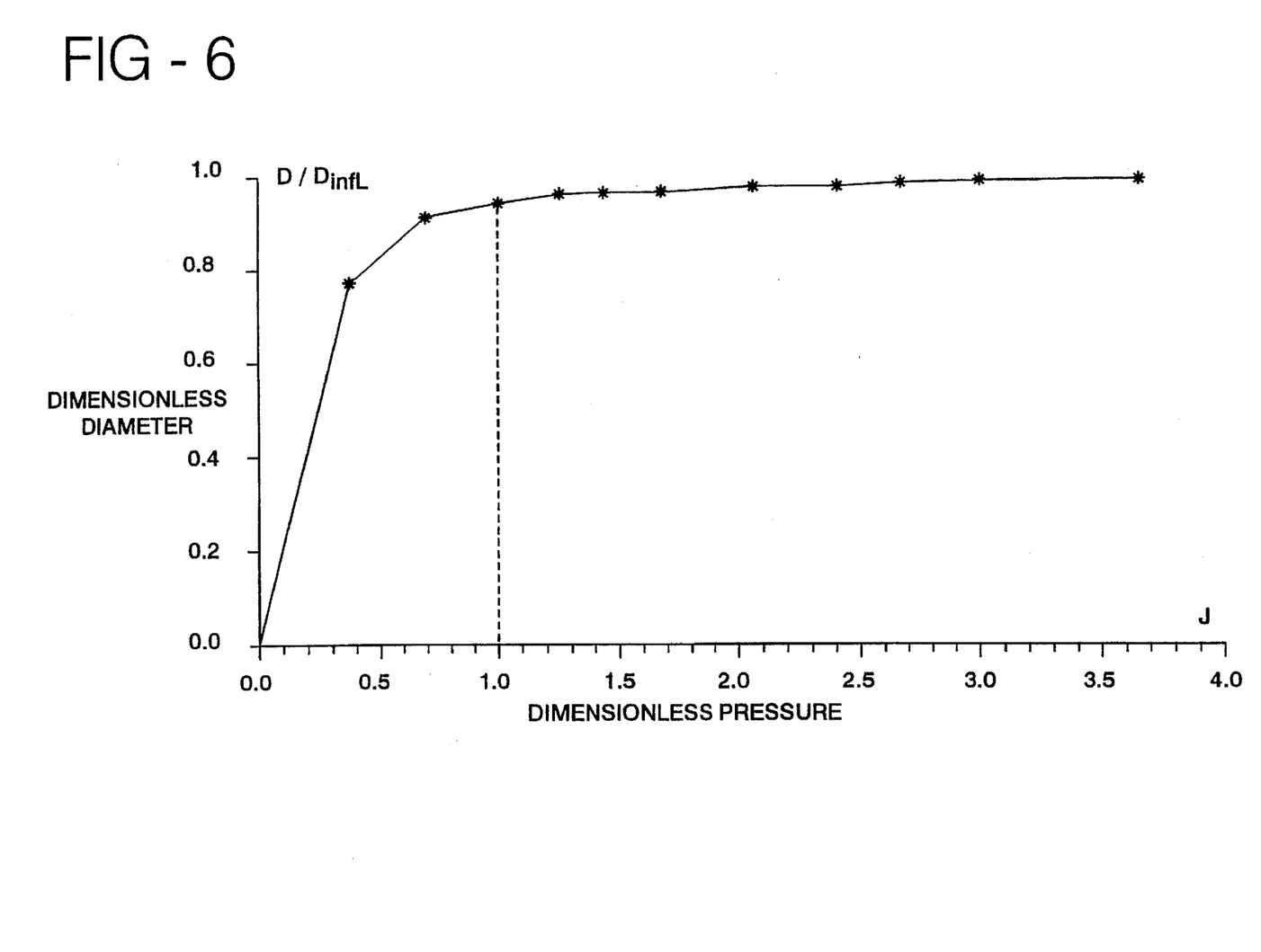
FIG. 6 is a graphical representation of dimensionless diameter vs. dimensionless pressure for a given balloon.

Thus, the proposed working pressure of 1.2 MPa will provide a fully expanded and non-compliant balloon. The inflation characteristics, diameter vs. J, of the above balloon are graphically depicted in FIG. 6. It is seen that for J>1, corresponding to approximately 0.4 MPa, the full diameter is reached within 5%. It would be meaningful to label a working pressure between 0.4 MPa to 1.2 MPa and claim non-compliance within this range, in accordance with the J-criteria.

Although illustrative embodiments of the present invention have been described herein with reference to accompanying drawings, it is to be understood that the invention is not limited to those precise embodiments, and that various other changes and modifications may be effected therein by one skilled in the art without departing from the scope or spirit of the invention.

What is claimed is:

1. A balloon for securement to a catheter comprising:

a resiliently elastomeric generally hollow pressure expandable body having a wall thickness of and being expandable under an internally applied minimum working pressure P from an unexpanded diameter $D_{defl}$ to an expanded diameter $D_{infl}$ said elastomeric body having a decant modules $E_{sec}$ where $$E_{sec} = \frac{\sigma(\epsilon_{infl})}{\epsilon_{infl}}$$

where $\sigma(\epsilon_{infl})$ is the nominal uniaxial tension in said body as a function of $\epsilon_{infl}$ and $$\epsilon_{infl} = \frac{D_{infl}}{D_{defl}} \text{; and}$$

a substantially non-compliant expandable, constraining structure affixed to said elastomeric body, said constraining structure being formed of fibers having an elongation to break of less than about 10% and a tensile strength greater than about 1 GPa and being selected from the group consisting of aramide, polyethylene, steel, polyester, glass, carbon, ceramics and liquid crystal polymers, said constraining structure limiting expansion of said body to a maximum diameter of $D_{infl}$ wherein said minimum working pressure P required to expand said body to a diameter no greater than $D_{infl}$ is defined by the question:

$$\frac{P \cdot D_{defl}}{2 \cdot E_{sec} \cdot t} \geq 1$$

2. The balloon of claim 1, wherein said constraining structure includes a plurality of helically spiralling layers positioned to balance torsional moments introduced into said elastomer.

3. The balloon of claim 2, wherein said helically spiralling layers are symmetrically arranged with respect to an imaginary midplane between said layers.

4. The balloon of claim 3, wherein said constraining structure includes helically extending inner and outer layers and two helically extending intermediate layers, and wherein said inner and outer layers are wound in one direction and said intermediate layers are wound in an opposite direction.

5. The balloon of claim 2, wherein said constraining structure includes helically extending inner, outer and intermediate layers, wherein said inner and outer layers have a winding direction opposite the winding direction of said intermediate layer, and wherein said intermediate layer has a thickness twice the thickness of the inner and outer layers.

6. The balloon of claim 1, wherein said constraining structure comprises a single layer of fibers.

7. The balloon of claim 4, wherein said single layer of fibers is braided.

8. The balloon of claim 1, wherein $E_{sec}$ is less than about 7 MPa at 500% elongation as measured in accordance with ASTM D412-87.

9. The balloon of claim 1 wherein said fibers are formed of a liquid crystal polymer.

* * * * *

UNITED STATES PATENT AND TRADEMARK OFFICE
CERTIFICATE OF CORRECTION

PATENT NO. : 5,647,848
DATED : July 15, 1997
INVENTOR(S) : Jørgensen

It is certified that error appears in the above-indentified patent and that said Letters Patent is hereby corrected as shown below:

At column 6, line 62, delete "It is seen that for J>1," and insert therefor --It is seen that for $J \geq 1$,--.

At column 7, line 15, delete "having a decant modules $E_{sec}$" and insert therefor --having a secant modules $E_{sec}$--.

Signed and Sealed this

Second Day of December, 1997

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,647,848
DATED : July 15, 1997
INVENTOR(S) : Jørgensen

It is certified that error appears in the above-indentified patent and that said Letters Patent is hereby corrected as shown below:

At column 7, line 17, delete $$``\ E_{sec} = \frac{6(\epsilon_{inf})}{\epsilon_{infl}}\ "$$

and insert therefor $$-- \ E_{sec} = \frac{\sigma(\epsilon_{infl})}{\epsilon_{infl}} \ --.$$

Signed and Sealed this

Sixth Day of January, 1998

Attest:

BRUCE LEHMAN

*Attesting Officer*     *Commissioner of Patents and Trademarks*